(12) United States Patent
Clauda et al.

(10) Patent No.: US 9,949,786 B2
(45) Date of Patent: Apr. 24, 2018

(54) SURGICAL DEVICES HAVING REMOVABLE BLADE AND JAWS

(71) Applicant: Ethicon LLC, Guaynabo, PR (US)

(72) Inventors: Phillip Clauda, Blue Ash, OH (US); John Hibner, Mason, OH (US); Adam Brown, Lebanon, OH (US)

(73) Assignee: Ethicon LLC, Guaynabo, PR (US)

( * ) Notice: Subject to any disclaimer, the term of this patent is extended or adjusted under 35 U.S.C. 154(b) by 555 days.

(21) Appl. No.: 14/598,671

(22) Filed: Jan. 16, 2015

(65) Prior Publication Data
US 2016/0206366 A1   Jul. 21, 2016

(51) Int. Cl.
| A61B 18/12 | (2006.01) |
| A61B 18/14 | (2006.01) |
| A61B 17/295 | (2006.01) |
| A61B 17/00 | (2006.01) |

(52) U.S. Cl.
CPC ........ *A61B 18/1445* (2013.01); *A61B 17/295* (2013.01); *A61B 2017/00477* (2013.01); *A61B 2018/1455* (2013.01)

(58) Field of Classification Search
CPC ...... A61B 2017/2931; A61B 2017/294; A61B 17/285; A61B 18/1447; A61B 2018/1452
See application file for complete search history.

(56) References Cited

U.S. PATENT DOCUMENTS

| 6,500,176 B1 * | 12/2002 | Truckai | A61B 18/1445 606/205 |
| 8,298,232 B2 | 10/2012 | Unger | |
| 8,864,795 B2 * | 10/2014 | Kerr | A61B 18/1442 606/167 |
| 2010/0292691 A1 * | 11/2010 | Brogna | A61B 18/1445 606/45 |
| 2012/0083835 A1 | 4/2012 | Shelton, IV et al. | |
| 2013/0161374 A1 | 6/2013 | Swayze et al. | |
| 2016/0166315 A1 * | 6/2016 | Boudreaux | A61B 18/1445 606/34 |

* cited by examiner

*Primary Examiner* — Daniel Fowler
(74) *Attorney, Agent, or Firm* — Mintz Levin Cohn Ferris Glovsky and Popeo, P.C.

(57) ABSTRACT

Surgical devices are provided having end effectors including a jaw closure. The devices herein generally include a handle portion, an elongate shaft, and an effector having first and second jaws configured to engage tissue. In some embodiments, the devices can be configured to allow for the removal of the upper jaw and the cutting blade when the device is not in use. In certain aspects, the jaw and/or cutting blade can be cleaned, sterilized, and reused or completely replaced. In some aspects, the device can then be reassembled including the cleaned or new elements, and reused.

14 Claims, 8 Drawing Sheets

SURGICAL DEVICES HAVING REMOVABLE BLADE AND JAWS

FIELD

The present invention relates to surgical devices and methods for transecting or cutting tissue, and methods of removing parts of a surgical device for cleaning and replacement.

BACKGROUND

Surgical devices are used in various open, endoscopic, and laparoscopic surgeries to transect tissue volumes and blood vessels. The devices generally include jaws for grasping tissue therebetween and a cutting mechanism that is advanced through the grasped tissue to transect it. The cutting mechanism can be designed to travel within a track formed in one or both jaws of the device. In some instances the devices can also be used to seal tissue volumes and blood vessels being transected. Electrodes can be disposed on a face of one or both of the jaws and can apply energy to the grasped tissue to promote hemostasis.

Further, the devices can generally include a handle with a closure actuator used to open and close the jaws, and a shaft allowing for mechanical linkage between the handle and the jaws. Some of these surgical devices incorporate mechanical linkages between a closure actuator and the jaws such that when a user manipulates the closure actuator, e.g., by manually squeezing a trigger, the jaws close.

One issue that can plague tissue cutting devices is that the cutting mechanism and jaws, including the electrode, need to be cleaned or replaced prior to reuse. More particularly, blades can become worn, dull, and should be replaced, and dirt and debris can build up between the jaws, and thus the jaws need to be cleaned and sterilized, or replaced. Existing devices are difficult to clean and sterilize for reuse because it can be complicated and cumbersome to clean, remove, and replace their parts. As a result, often the entire end effector is replaced prior to a subsequent surgical use.

Accordingly, there remains a need for improved surgical devices and methods for compressing tissue and sensing tissue and other objects grasped by the device including surgical devices that can be easily cleaned and/or elements of the device that can be easily replaced.

SUMMARY

Desired benefits of the disclosed devices include easily removing components to clean and/or replace them, and easily reassembling the devices with clean and/or replaced components. Surgical devices, systems, and methods for compressing tissue and/or sensing tissue and other objects grasped by the device are provided herein.

In one exemplary embodiment a surgical device includes a first jaw, a second jaw removably and pivotally coupled to the first jaw, and a cutting blade slidably coupled to the first and second jaws. The first jaw can have a first surface and an opposed second surface, with the first surface having a tissue engaging portion disposed at least at a distal portion of the first jaw. The jaw can also include an opening formed in its proximal portion, with the opening extending through the first jaw from the first surface to the second surface. The second jaw can also have a first surface and an opposed second surface, with the first surface having a tissue engaging portion disposed at least at a distal portion of the second jaw. The first surfaces of the first and second jaws can be opposed to each other to grasp tissue therebetween. The cutting blade can have opposed first and second ribs disposed at its distal portion, with the first rib being configured to slide along the second surface of the first jaw and the second rib being configured to slide along the second surface of the second jaw. As a result, distal advancement of the first and second ribs along the second surfaces of the first and second jaws moves the second jaw towards the first jaw into a closed position, and proximal retraction of the first and second ribs along the second surfaces of the first and second jaws allows the second jaw to pivot away from the first jaw into an open position. A perimeter of the first rib can be less than a perimeter that defines the opening in a proximal end of the first jaw such that the first rib is configured to be selectively passed through the opening to disassociate the cutting blade from the first jaw.

In some embodiments, the surgical device can include a handle portion and a shaft extending distally from the handle portion. A distal end of the shaft can be fixedly coupled to a proximal end of first jaw. The handle portion can also include an actuating trigger, a stationary grip, and a button. The actuating trigger can be operably coupled to the cutting blade such that advancing the trigger towards the stationary grip advances the cutting blade distally and advancing the trigger away from the stationary grip retracts the cutting blade proximally. The button can be coupled to the actuating trigger such that the button is configured to initiate an overextended mode in which the trigger advances further away from the stationary handle to dispose the distal end of the cutting blade in the shaft. Further, the device can include a push rod disposed in the shaft, with a proximal end of the cutting blade being removably coupled to a distal end of the push rod. The distal end of the cutting blade can be configured to be disposed in the shaft so that second rib does not engage the second surface of the second jaw and allows the second jaw to be decoupled from the first jaw.

In some embodiments, each of the first and second jaws of the device can have a centrally disposed channel formed in them, and the cutting blade can further include a main vertical body extending between the channels of the first and second jaws. The blade can be configured to translate through the centrally disposed channels of the jaws, and the main vertical body of the blade can have a cutting edge formed on its distal end, between the first and second ribs. The width of the first rib and a width of the second rib can be greater than a width of the main vertical body, the width being substantially perpendicular to a longitudinal axis extending through the main vertical body in a proximal to distal direction and substantially perpendicular to a height of the main vertical body that extends vertically between the first and second jaws. In some embodiments, the tissue engaging portion of the second jaw can further include an electrode.

In another exemplary embodiment of a surgical device, the device can include a handle assembly having a trigger, a shaft extending distally from the handle assembly and having a pusher assembly disposed therein, a jaw assembly coupled to a distal end of the shaft, and a cutting blade having a proximal end coupled to the pusher assembly and a distal end slidably coupled to first and second jaws of the jaw assembly. The pusher assembly can be operably coupled to the trigger, and the first and second jaws of the jaw assembly can be pivotally coupled together. The cutting blade can be configured to be advanced distally along the jaws by the trigger and pusher assembly to close the jaws. It can also be configured to retract proximally along the jaws to allow the jaws to open. The first jaw can be configured to be removably and replaceably coupled with the second jaw such that the first jaw can be decoupled from the second jaw, and the first jaw, for instance after it has been cleaned and sterilized, or a replacement first jaw, can subsequently be coupled to the second jaw. Further, the cutting blade can also be a removable and replaceable component. For example, the cutting blade can be removably and replaceably coupled with the pusher assembly such that the cutting blade can be decoupled from the pusher assembly and the cutting blade, for instance after it has been cleaned and sterilized, or a replacement cutting blade, can subsequently be coupled to the pusher assembly.

In some embodiments, the trigger can be configured to move between a first resting position at which the distal end of the cutting blade is disposed at a proximal end of the jaw assembly and a second cutting position at which the distal end of the cutting blade is disposed proximate to a distal end of the jaw assembly. In such embodiments, the trigger can be located more proximate to a stationary handle of the handle assembly in the second cutting position than in the first resting position. Further, in some embodiments, the trigger can move to a third, over-extended position at which the distal end of the cutting blade is disposed proximal to a proximal end of the jaw assembly. In such embodiments, the trigger can be located more proximate to the stationary handle in the first resting position than in the third, over-extended position. The trigger can also include a trigger actuator or button, which can be used, for example, to initiate a supply of energy to an electrode associated with one or both jaws, and a cleaning button, which can be used, for example, to advance the trigger to the third, over-extended position.

Each of the first and second jaws can include a centrally disposed channel formed in the jaws. The cutting blade of the device can include a main vertical body extending between the channels of the first and second jaws, with the main vertical body being configured to translate through the channels. Further, the main vertical body can have a cutting edge formed on its distal end. The cutting blade can further include a first rib disposed in a longitudinal channel formed in the first jaw and a second rib disposed in a longitudinal channel formed in the second jaw. Each of the first and second ribs can have widths formed at distal ends thereof that are less than the widths of more proximal portions of the main vertical body, the width being substantially perpendicular to a longitudinal axis extending through the main vertical body in a proximal to distal direction and substantially perpendicular to a height of the main vertical body that extends vertically between the first and second jaws. In some embodiments, the tissue engaging portion of one or both jaws can include an electrode.

In one exemplary embodiment of a method for removing a cutting blade from the surgical device, the method can include, retracting a distal end of a cutting blade of a surgical device proximal of a proximal end of a first jaw of a jaw assembly of the surgical device, detaching the first jaw from a second jaw of the jaw assembly, passing the distal end of the cutting blade through an opening extending through the second jaw, and detaching a proximal end of the cutting blade from an actuation assembly of the surgical device. In some embodiments, prior to passing the distal end of the cutting blade through an opening extending through the second jaw, the method can include advancing the distal end of the cutting blade distally past the opening, and retracting the distal end of the cutting blade to pass the distal end through the opening.

Further, in some embodiments, detaching a proximal end of the cutting blade from an actuation assembly can optionally occur after advancing the distal end of the cutting blade distally past the opening but prior to retracting the distal end of the cutting blade to pass the distal end through the opening. In still other embodiments, advancing the distal end of the cutting blade distally past the opening can further include advancing the distal end of the cutting blade proximate to a distal end of the jaw assembly.

The method can include reassembly of the end effector by adding a new cutting blade and/or jaw to the surgical device, or cleaning and sterilizing the removed blade and/or jaw and reusing it upon reassembly. The reassembly method can include coupling one of the proximal end of the cutting blade or a proximal end of a new cutting blade to the actuation assembly, and coupling one of the first jaw or a new first jaw to the second jaw of the jaw assembly. The trigger of the surgical device can be advanced towards a handle of the surgical device to effect the coupling of the first jaw or new first jaw to the second jaw of the jaw assembly. In some embodiments, retracting a distal end of a cutting blade of a surgical device proximal to a proximal end of a first jaw of a jaw assembly can include advancing a trigger of the surgical device further away from a handle of the surgical device than the trigger is located when it is at a resting position at which the cutting blade is coupled to a proximal end of the jaw assembly.

BRIEF DESCRIPTION OF THE DRAWINGS

This invention will be more fully understood from the following detailed description taken in conjunction with the accompanying drawings, in which.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments provided for herein or otherwise derivable therefrom. Such modifications and variations are intended to be included within the scope of the present invention. Additionally, to the extent features or sides of a structure are described herein as being a "first feature" or "first side" or a "second feature" or "second side," such numerical ordering is generally arbitrary, and thus such numbering can be interchangeable.

The terms "proximal" and "distal" are used herein with reference to a clinician manipulating the handle portion of the surgical instrument. The term "proximal" referring to the portion closest to the clinician and the term "distal" referring to the portion located away from the clinician. It will be further appreciated that, for convenience and clarity, spatial terms such as "vertical," "horizontal," "up," and "down" may be used herein with respect to the drawings. However, surgical instruments are used in many orientations and positions, and these terms are not intended to be limiting and/or absolute. Further, a person skilled in the art will recognize that a number of different terms can be used interchangeably while still being understood by the skilled person. By way of non-limiting example, the terms "cut" and "transect" are generally used interchangeably herein.

The present disclosure generally relates to surgical devices and methods for transecting tissue or blood vessels, collectively referred to herein as "tissue." The devices, also referred to herein as instruments, disclosed or otherwise derivable from the disclosures herein include various features for allowing removal of the cutting blade mechanism and at least one jaw to allow for cleaning and sterilization, or replacement, before reuse of the device. For example, in one exemplary embodiment, the device can be configured to allow the cutting element to be retracted so that it becomes disassociated from the jaws, which in turn allows at least one of the jaws to be removed from the device. The cutting element can be further manipulated to remove it entirely from the device as well. The removed components can then be cleaned, sterilized, and re-associated with the device for future use, or they can be disposed of and replaced by a new, sterilized jaw and/or cutting element for use as part of the device.

Surgical Devices

Surgical devices that can be used in conjunction with the present disclosures can come in a variety of configurations. Often they can generally include a handle portion, an elongate shaft, and an end effector having first and second jaws configured to engage tissue therebetween. The end effector can include a cutting blade mechanism, such as an I-blade, disposed between the jaws, and can further include an electrode disposed on one or both jaws. In some embodiments, one jaw can be removable to allow removal and cleaning, or replacement, of the jaw, I-blade, and/or electrode.

Figure 1:
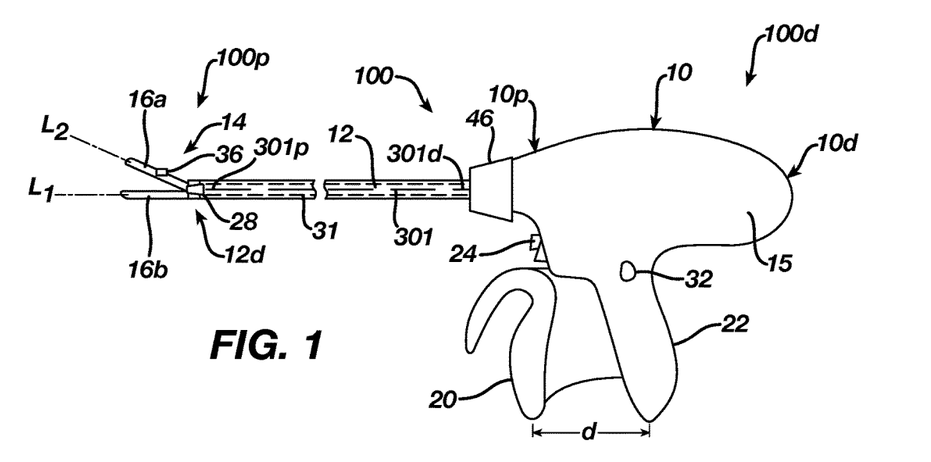
FIG. 1 is a side view of an exemplary surgical device having an end effector.

FIG. 1 illustrates one embodiment of a surgical device 100 configured to grasp and cut tissue. The surgical device 100 generally includes a proximal handle portion 10, a shaft portion 12, and an end effector 14 for grasping tissue. The proximal handle portion 10 can be designed to operate various features of the end effector 14. For example, the proximal handle portion 10 can close and open a jaw assembly of the end effector 14 to grasp tissue. The jaw assembly can include jaws 16a, 16b that are configured to pivot with respect to each other to grasp tissue disposed therebetween. By way of further non-limiting example, the proximal handle portion 10 can initiate the supply of electrical energy to one or more electrodes 36 associated with either or both of the jaws 16a, 16b, to weld or otherwise seal portions of the grasped tissue. The components to initiate these actions can be part of the proximal handle portion 10 and can extend through or be electrically or mechanically coupled to components that extend through the shaft portion 12. The shaft portion 12 extends distally from the proximal handle portion 10 and can have a bore 31 extending therethrough for carrying mechanisms for actuating jaws 16a, 16b of the end effector 14. For example, a push rod 301 can extend through the bore 31 of the shaft portion 12 to connect the proximal handle portion 10 to the end effector 14. A proximal end of the push rod 301 can be coupled to the handle portion 10 using any known mechanical means for connection, and a distal end 301d of the push rod can be coupled to a cutting blade mechanism 28 associated with the end effector 14. Preferably, the bore 31 in the shaft portion 12 is greater than the size of the cutting blade mechanism 28, so that the cutting blade mechanism 28 can easily be retracted into the bore 31. Further, the proximal handle portion 10 can also be configured to operate other components that work in conjunction with the end effector 14, such as a cutting blade mechanism 28 that extend through a portion of the shaft 12 and is configured to cut tissue grasped by the jaws 16a, 16b. Components of this nature are known to those skilled in the art, and thus further elaboration related to aspects such as how user energy is translated from the handle portion 10 to the cutting blade mechanism 28 and end effector 14 is unnecessary.

The handle portion 10 can have any type of design known in the art for operating end effectors 14. In an illustrated embodiment, the handle portion 10 has a pistol-grip configuration that includes a housing 15, an actuating trigger 20, and a stationary grip 22. Movement of the actuating trigger 20 towards the stationary grip 22 can be effective to perform a variety of functions. In the illustrated embodiment, movement of the actuating trigger 20 is effective to close the jaws 16a, 16b and cut tissue disposed between the jaws using a push rod 301 and cutting blade mechanism 28. In some embodiments, the actuating trigger 20 can move through two separate cycles or strokes to perform these functions. For example, the actuating trigger 20 can move through a first cycle or stroke in which it first moves from an initial position as shown in FIG. 1 and towards the stationary grip 22 and then returns back to its initial position, which is effective to advance the cutting blade mechanism 28 to close the jaws. The actuating trigger 20 can then move through a second cycle or stroke, again moving from the initial position and towards the stationary grip 22 and then returning back to its initial position, which is effective to advance the cutting blade mechanism 28 through at least a portion of the jaws 16a, 16b to cut tissue disposed therebetween. While a variety of configurations can be used to allow movement of the actuating trigger 20 to translate into distal advancement of the cutting blade mechanism 28, as described in further detail below, the actuating trigger 20 can be effective to distally advance a push rod 301 coupled to a cutting blade mechanism 28, such that axial movement of the push rod 301 in the distal and proximal directions results in axial movement of the cutting blade mechanism 28 in distal and proximal directions as well. Accordingly, as the actuating trigger 20 returns to the initial position during the second stroke, the cutting blade mechanism can retract proximally with respect to the jaws. The actuating trigger 20 can be movable manually or electronically.

A cleaning button 32 disposed on the handle can allow the actuating trigger 20 to be moved distally away from the stationary grip 22 such that the distance between the trigger 20 and grip 22 is even greater than it is in the initial position. This allows the cutting blade mechanism 20 to be retracted proximally even further, for example retracting completely into the bore 31 of the shaft 12. Complete retraction of the cutting blade mechanism 28 into the bore 31 in the shaft 12 allows the top jaw 16a to be removed from the end effector 14, as discussed further below. The cleaning button 32 can be coupled to the actuating trigger 20 using any mechanical means that allow the cleaning button 32 to control the movement of the actuating trigger 20 away from and/or towards the stationary grip 22. Further, the location of the cleaning button 32 in the illustrated embodiment is not limited, as it can be disposed anywhere on the handle portion 10 that will mechanically allow for a connection to the actuating trigger 20 to allow distal movement thereof. A person skilled in the art will recognize other actuators besides a button that can be associated with the trigger 20 to assist in moving it into an over-extended position so that the cutting blade mechanism 28 can be disposed within the shaft 12 and the upper jaw 16a and/or cutting blade mechanism 28 can be removed.

The illustrated embodiment also includes an actuator, e.g. an actuator button 24, as part of the handle portion 10. The actuator button 24 can be configured such that pressing it completes a circuit to power the electrode(s) 36 to seal tissue disposed in the jaws 16a, 16b. More particularly, completion of the circuit by the actuator button 24 allows electrical energy to pass from a power source disposed in the housing 15, through one or more electrical leads (not shown), and to the electrode 36. The electrical lead can be disposed in the shaft 12 to electrically connect the button 24 and the electrode 36. Although the power source is described as being in the housing 15, in other embodiments the power source can be external of the housing 15 and the housing 15 can be configured to electrically connect to the power source, for instance by way of a socket extending from the housing 15 to connect to the power source. Similar to the actuating trigger 20, a person skilled in the art will recognize that the actuator can have a variety of other designs, and can perform a variety of other types of functions, without departing from the spirit of the present disclosure. By way of non-limiting example, in some embodiments the actuator button 24 can also be used to actuate the cutting blade mechanism 28 through at least a portion of the jaws 16a, 16b.

Other features to assist in moving and actuating the components of the device 100 can also be incorporated into the proximal handle portion 10. By way of example, the handle portion 10 can include a rotatable knob 46 disposed at a distal end 10d of the handle portion 10 to facilitate rotation of the shaft 12, and thus the end effector 14 coupled thereto, with respect to the handle portion 10 around a centrally disposed longitudinal axis $L_1$ of the shaft 12. A person skilled in the art will recognize other non-limiting examples of features that can be incorporated with the handle portion 10 to assist in manipulating or otherwise operating the device include: (1) an articulation lever for articulating the end effector 14; (2) a retraction handle for retracting the cutting blade mechanism 28 towards and/or to positions such as those related to the initial position and the over-extended position in place of or independent of any retraction that is part of a firing stroke initiated by the actuating trigger 20 or other component, or a retraction stroke initiated by the cleaning button 32 or other component; (3) a firing lockout assembly to prevent the cutting blade mechanism 28 from being actuated at an undesirable time; and (4) an emergency return button to retract the cutting blade mechanism 28 before a firing stroke is completed, for instance in a case where completing the firing stroke may cause tissue to be undesirably cut. Although features such as an articulation lever, a retraction handle, a firing lockout assembly, and an emergency return button are not explicitly illustrated in the device 100, a person skilled in the art will recognize a variety of configurations for each feature that can be incorporated into the handle portion 10 and/or other portions of the device 100 without departing from the spirit of the present disclosure.

The shaft 12 can be removably coupled to the distal end of the handle portion 10 and the shaft 12 can include a bore 31 extending therethrough for passing mechanisms to help actuate the jaws 16a, 16b or to perform other functions at the surgical site. In the described embodiment, a push rod 301 extends through the bore 31, towards the distal end 100d of the device 100, and is coupled to the cutting blade mechanism 28, and leads are disposed in the shaft and create an electrical connection between the actuation button 24 and the electrode 36. The push rod 301 can be coupled to components of the handle portion 10 such that actuation of the components of the handle portion 10 translate to actuation of the push rod 301 and cutting blade mechanism 28. A distal end of the shaft 12 can be configured to receive the end effector 14 by any known means for coupling an end effector to a shaft, including by a removable connection that allows various end effectors to removably and replaceably be coupled to the distal end. A proximal portion of the shaft 12 can be configured to receive the proximal handle portion 10 by a removable connection that allows various shafts to removably and replaceably be coupled to the handle portion, or vice versa. While the shaft 12 can have any number of shapes and configurations, depending, at least in part, on the configurations of the other device components with which it is used and the type of procedure in which the device is used, in the illustrated embodiment the shaft 12 is generally cylindrical and elongate.

The illustrated embodiment of a surgical stapling instrument 100 provides one of many different configurations, and associated methods of use, that can be used in conjunction with the disclosures provided herein. Additional, non-limiting exemplary embodiments of surgical staplers, components thereof, and their related methods of use, that can be used in accordance with the present disclosure include those devices, components, and methods provided for in U.S. Pat. No. 8,298,232, U.S. Patent Application Publication No. 2012/0083835 and U.S. Patent Application Publication No. 2013/0161374, each of which is incorporated by reference herein in its entirety. While the illustrated embodiment includes features for sealing tissue, in other embodiments the surgical device can be configured to grasp and cut tissue without including a sealing feature.

End Effector

Figure 2:
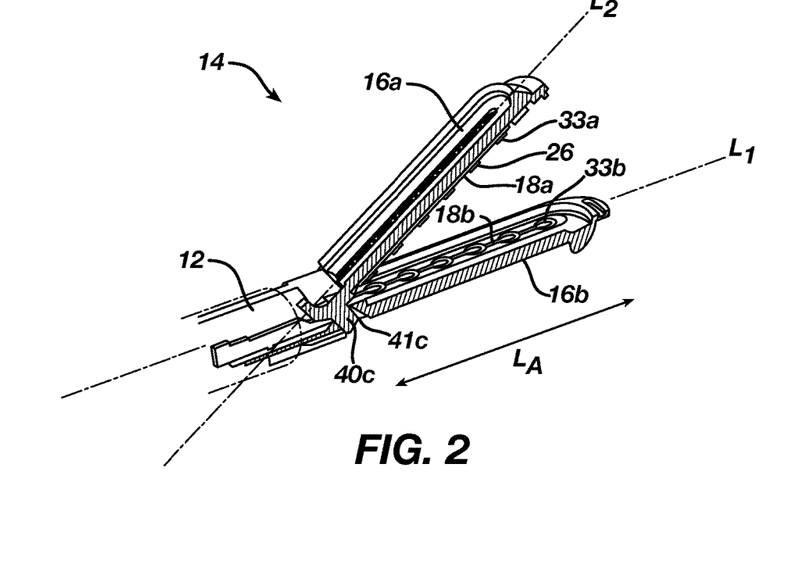
FIG. 2 is a perspective view of the end effector of FIG. 1 in which the jaws are in an open position.

The end effector 14 can have a variety of sizes, shapes, and configurations. As can be seen in FIG. 2, the end effector 14 can include a first, upper jaw 16a and second, lower jaw 16b, one or both of which can be configured to close or approximate about an axis $L_1$. Both of the jaws 16a, 16b can be movable relative to the shaft portion 12, or alternatively, a single jaw can rotate to move the end effector 14 between a first, open position in which the jaws 16a, 16b are positioned a distance apart from each other, and a second, closed position in which the jaws 16a, 16b are substantially opposed to each other. When the jaws 16a, 16b are in the second, closed position, a longitudinal axis $L_2$ of the upper jaw 16a can be substantially parallel to a longitudinal axis $L_1$ of the lower jaw 16b and the jaws 16a, 16b can be in direct contact. In the illustrated embodiment, the upper jaw 16a can pivot relative to the shaft portion 12 and relative to the lower jaw 16b while the lower jaw 16b remains stationary, that is the lower jaw 16b can be fixedly coupled to the shaft portion 12.

Figure 3A:
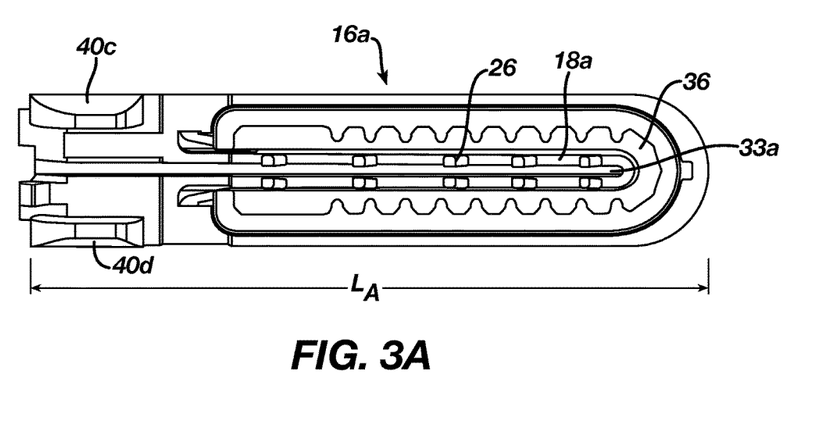
FIG. 3A is a bottom view of the upper jaw of the end effector of FIG. 2 with an electrode disposed thereon.
Figure 3B:
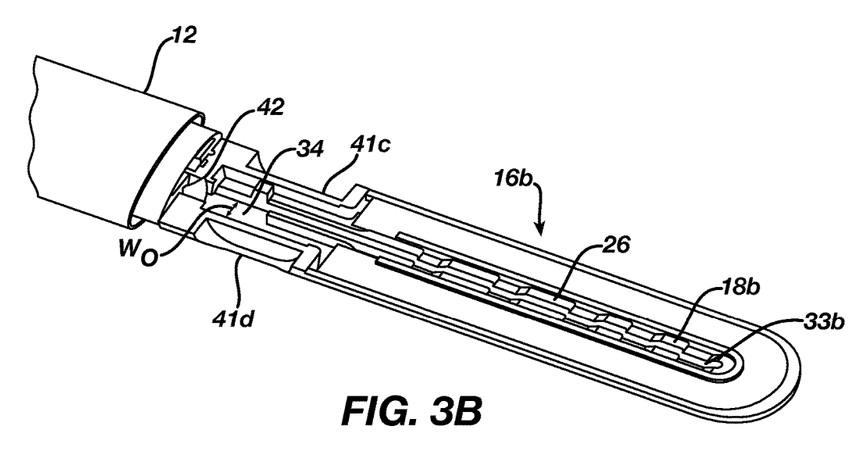
FIG. 3B is a top perspective view of the bottom jaw of the end effector of FIG. 2.

The top and bottom jaws 16a, 16b can be pivotally connected using a number of known configurations. In the illustrated embodiment, the jaws 16a, 16b are connected by a hinge mechanism that allows the top jaw 16a to pivot with respect to the bottom jaw 16b. The bottom jaw 16b can be attached to the shaft 12 by a mechanical connection such as welding as shown in FIG. 3B, but other attachment means are possible, including a connection that allows the lower jaw to be removable. Grooves 41c, 41d can be disposed on the bottom jaw 16b to accept rounded protrusions 40c, 40d on the top jaw. The interaction between the grooves 41c, 41d and the protrusions 40c, 40d allow the top jaw 16a to open and close with respect to the bottom jaw 16b while being removably coupled to the bottom jaw 16b using the cutting blade mechanism 28. While the size and shape of the grooves 41c, 41d and protrusions 40c, 40d can take any number of configurations, in the illustrated embodiment the protrusions 40c 40d are substantially hemispherical and the grooves 41c, 41d are complimentary in shape so that the protrusions 40c, 40d can sit within the grooves 41c, 41d.

Figure 8A:
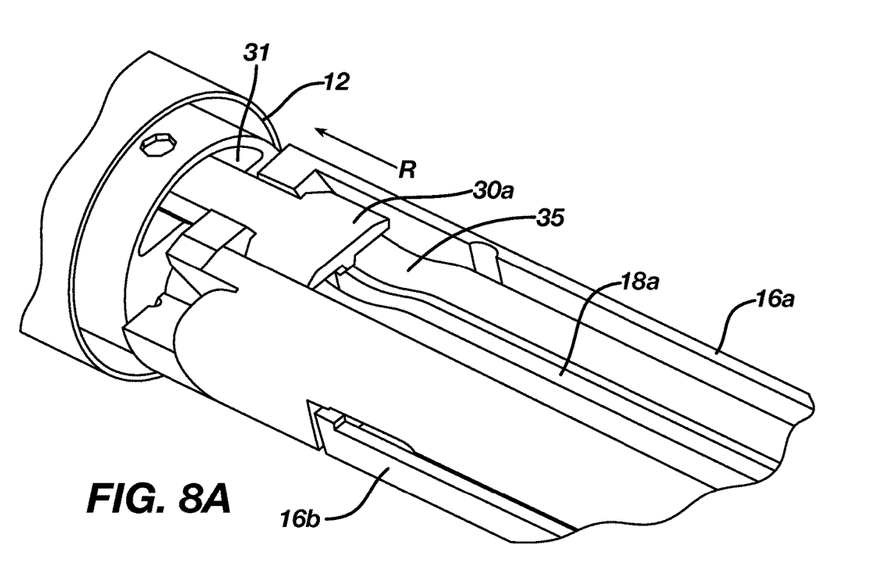
FIG. 8A is a perspective view of the cutting blade mechanism of FIG. 3A being disposed at an initial position, in which the cutting blade mechanism is coupled to each of upper and lower jaws of the device of FIG. 1.

Tracks 33a, 33b for receiving a cutting element can be centrally disposed with respect to a width of each jaw 16a, 16b. FIG. 3A shows a top jaw 16a with a track 33a formed in the top jaw 16a, and FIG. 3B shows a track 33b formed in the bottom jaw 16b. In the illustrated embodiment, the tracks 33a, 33b are formed in the opposed faces of the jaws 18a, 18b and extend through a portion of the jaws, towards their respective top and bottom surfaces. Each track can be generally elongate having a length that extends a substantial portion of a length of the jaws, a width that is wider than a total thickness of the cutting blade mechanism 28 configured to be disposed therein, and a depth that is deep enough to receive the cutting blade mechanism 28 disposed therein. As shown in FIG. 8A, the top jaw 16a can preferably include a ramp 35 in the track 33a that extends towards the top surface of the top jaw 16a that prevents the cutting blade mechanism from accidentally retracting proximally into the shaft and accidentally releasing the top jaw. The shape, length, width, and depth of the tracks 33a, 33b can depend on a variety of different factors, including, by way of non-limiting example, the dimensions of the cutting blade mechanism and jaws and the type of procedure with which the device will be used. A person skilled in the art will recognize any number of track configurations that can be used in conjunction with the disclosures provided for herein.

In an illustrated embodiment, the bottom jaw can include an opening 34, shown in FIG. 3B, which can be configured to accept a rib of the cutting blade mechanism and allow removal of the cutting blade mechanism when the top jaw is removed, as described further below. The opening 34 can be positioned on the proximal end of the track 33b in the bottom jaw 16b. In an illustrated embodiment, a ramp 42 can be positioned proximally to the opening 34 to prevent the cutting blade mechanism 28 from falling into the opening 34 when advanced distally. The ramp 42 should be of a size and configuration sufficient to allow the distal end of a cutting blade mechanism 28d to pass over the opening 34 without allowing the bottom rib 30b to fall into the opening 34. Further, the ramp 42 should be of a size and configuration to allow passing of a cutting blade mechanism 28 distally through the bore 301 in the shaft 12.

The jaws 16a, 16b can have any combination of features configured to facilitate grasping, cutting and sealing tissue therebetween. The first jaw 16a can have a first inner engagement surface 18a and the second jaw 16b can have a second inner engagement surface 18b, both of the first and second engagement surfaces 18a, 18b being configured to directly contact tissue. Either one or both of the engagement surfaces 18a, 18b can include one or more surface features formed thereon that can help secure the tissue thereon. For example, the surface features can include various surface features, such as teeth, ridges, or depressions, configured to increase friction between the tissue and the engagement surfaces 18a, 18b of the jaws 16a, 16b without tearing or otherwise damaging the tissue in contact with such surface features. FIGS. 2, 3A, and 3B illustrate a plurality of teeth 26 positioned along an axial length of both of the engagement surfaces 18a, 18b and can facilitate grasping tissue and forming substantially smooth, uniform layers of tissue to improve tissue effect.

Figure 7:
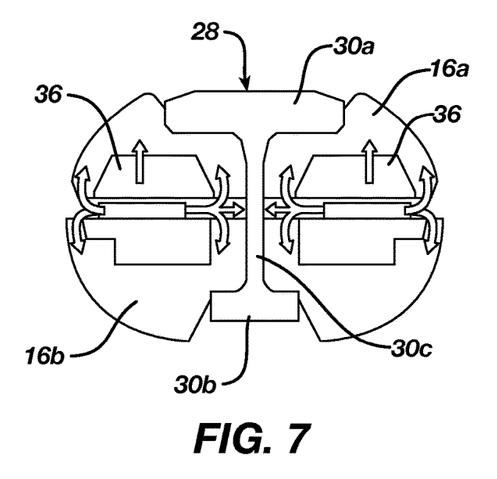
FIG. 7 is a schematic cross-sectional front view of tissue engaged between the jaws of the end effector of FIG. 6.

One or both jaws can further include elements that allow for the transfer of energy to tissue. For example, electrodes can be used to transfer energy to tissue and assist in hemostasis. In exemplary embodiments, elements such as one or more electrodes are present on at least one of the tissue engaging surfaces 18a, 18b. FIGS. 3A and 7 show an electrode 36 disposed on the tissue engaging surface 18a of the top jaw 16a. In some exemplary embodiments, the electrode 36 can made from a positive temperature coefficient (PTC) polymer or matrix that provides homogeneous and precisely regulated energy delivery with low thermal spread. The PTC conductive-resistive matrix can be a variably resistive body that comprises a polypropylene or a medical grade silicone polymer that is doped with conductive particles (e.g., carbon). Polymer PTC materials are known in the field of over current protection devices that will "trip" and become resistant when a selected trip current is exceeded. Although in the illustrated embodiment the electrode 36 is a single electrode that is associated with the top jaw 16a, in other embodiments multiple electrodes can be used, and one or more electrodes can be disposed on either or both of the upper and lower jaws 16a, 16b.

Figure 6:
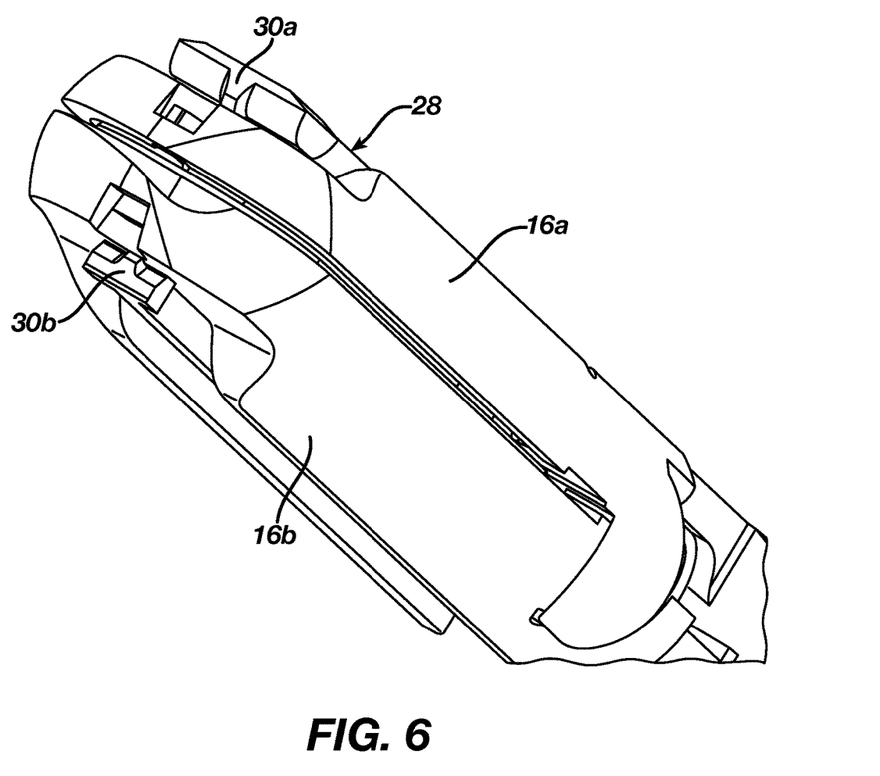
FIG. 6 is a perspective view of the jaws of the end effector of FIG. 2 in a closed position and including the cutting element of FIG. 3A associated therewith.

One jaw can be removable from the end effector. In an illustrated embodiment, the upper jaw 16a is removable from the end effector 14. That is, in an illustrated embodiment the upper jaw 16a is removably coupled to the lower jaw 16b. As shown in FIGS. 6 and 8A, the upper jaw 16a is coupled to the lower jaw 16b by the cutting blade mechanism 28 disposed in the tracks 33a, 33b. When the cutting blade mechanism is proximally retracted completely into the bore 31 in the shaft 12 such that it no longer engages the upper and lower jaws 16a, 16b, the upper jaw 16a can be removed from the end effector. Often the electrode 36 is the first component of an end effector to wear out and require replacement. When the electrode 36 is disposed on the removable jaw, the electrode 36, or the entire jaw 16a, can be replaced. Electrodes disposed on the lower jaw 16b, can also be more easily removed and replaced due to the removable nature of the upper jaw providing better access to the bottom jaw.

A person skilled in the art will appreciate that the first and second jaws 16a, 16b can have any suitable shape and length for engaging tissue, with the shape, length, and overall configuration being selected, at least in part, based on the targeted anatomical structure for treatment and the other components with which the jaws 16a, 16b are being used. In the illustrated embodiment, the jaws 16a, 16b have a substantially elongate and straight shape, such that the midpoints of the proximal ends and the midpoints of the distal ends of the jaws are both disposed substantially along the longitudinal axis $L_1$. A person skilled in the art will appreciate that one or both of the jaws 16a, 16b can be curved along axes $L_1$ and $L_2$, or of any other suitable configuration. The jaws 16a, 16b can have any suitable axial length $L_A$ for engaging tissue, where the axial length $L_A$ is measured along the longitudinal axes $L_1$ and $L_2$, as shown in FIG. 2. The axial length $L_A$ of the jaws 16a, 16b can also be selected based on the targeted anatomical structure for transection and/or sealing of tissue. In the illustrated embodiment, the axial length $L_A$ of the upper and lower jaws 16a, 16b, is approximately equivalent.

Cutting Blade Mechanism

Figure 4A:
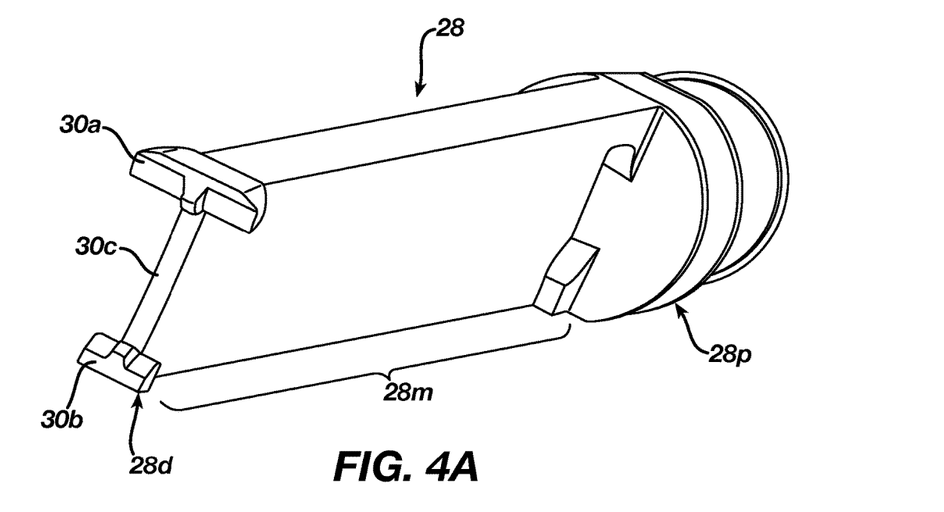
FIG. 4A is a side perspective view of a cutting blade mechanism of the device of FIG. 1.
Figure 4B:
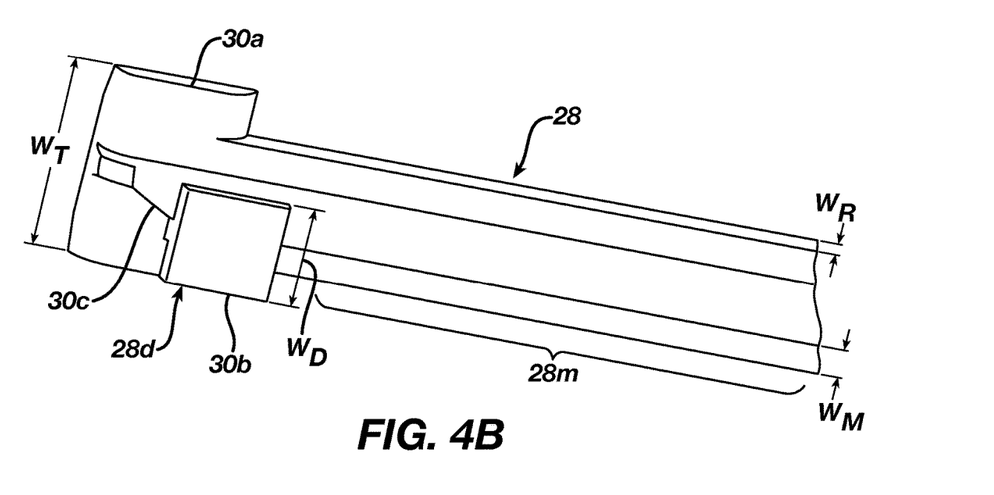
FIG. 4B is a bottom perspective view of the cutting blade mechanism of FIG. 3A.

FIGS. 4A and 4B show one exemplary embodiment of a cutting blade mechanism for use in the end effector 14 shown in FIG. 2. Any cutting blade that fits in the tracks in the top and bottom jaws of the end effector may be suitable for use in the end effector of FIG. 2. Notably, in some embodiments, the cutting blade mechanism also supplies a compressive force to the jaws to assist in their closure and in monitoring compression on tissue disposed between the jaws.

FIGS. 4A and 4B show an exemplary embodiment of a cutting blade mechanism. In a preferred embodiment, the cutting blade mechanism 28 is defined by a proximal end 28p, a distal end 28d, a top rib 30a, a bottom rib 30b, and opposed side surfaces. The opposed side surfaces form a substantial portion of a surface area of the cutting blade, thus giving it an "I" shape. The cutting blade mechanism can sometimes be referred to as an "I-Blade." The ribs 30a, 30b on the top and bottom of the cutting blade mechanism allow the blade to move proximally and distally through the tracks in the jaws in response to movement of the actuating trigger 20, without allowing the cutting blade mechanism to easily slide out of the tracks. In the illustrated embodiment, the cutting blade mechanism 28 has opposed top and bottom ribs 30a, 30b disposed at a distal portion of the cutting blade 28d, the top rib 30a can be configured to slide along the top jaw 16a, and the bottom rib 30b configured to slide along the bottom jaw 16b. Distal advancement of the ribs 30a, 30b along the jaws 16a, 16b can move the bottom jaw 16b towards the top jaw 16a into a closed position as shown in FIGS. 6 and 8A. Proximal retraction of the ribs 30a, 30b along the jaws allows the top jaw 16a to pivot away from the bottom jaw 16b into an open position.

The distal end 28d of the cutting blade mechanism can include a top rib 30a so that the cutting blade mechanism can be easily moved proximally and distally within the tracks 33a, 33b. The top rib can be of any configuration suitable to allow this movement within the jaws. The distal end of the top rib 30a can have a width $w_t$ be wider than a width $w_r$ of the remainder of the rib to provide compression to tissue, and prevent the cutting blade mechanism 28 from falling through the tracks 33a, 33b. In an illustrated embodiment, the top rib 30a is configured in a rectangular shape approximately perpendicular to the cutting edge 30c. The smallest length of the rectangle can be at least as wide as the track 33a in the top jaw 16a.

The distal end 28d of the cutting blade mechanism 28 can further include, on the bottom side, a bottom rib 30b configured so that the cutting blade mechanism 28 can both provide compression to tissue and be easily removed from the tracks 33a, 33b by way of the opening 34. More particularly, the bottom rib 30b, which is included only on the distal end 28d of the cutting blade mechanism 28 is preferably configured to fit through an opening in the bottom jaw 34, shown in FIG. 4. The bottom rib 30b should be at least wider than the track 33b in the bottom jaw to provide compression to tissue as the cutting blade mechanism 28 is advanced distally to cut tissue. This bottom rib 30b in conjunction with the opening in the bottom jaw 34 is configured to facilitate removal of the cutting blade mechanism 28 from the end effector 14, as further described below. As shown, in some embodiments, a width $w_b$ of the bottom rib 30b can be approximately equal to the width $w_r$ of the portion of the cutting blade mechanism 28 proximal of the rib 30a. The rib 30b can be formed by removing portions of the cutting blade mechanism 28 proximal of the rib 30b such that the width $w_b$ of the rib 30b is greater than a width $w_m$ of the portion proximal of the rib 30b, i.e., the portion illustrated as 28m. Notably, a width $w_o$ of the opening 34 can generally be at least slightly larger than the width wb of the bottom rib 30b so that the rib 30b can be passed through the opening 34 when disassociating the cutting blade mechanism 28 from the device 10. A length of the opening 34 is also such that the rib 30b can pass through the opening 34.

The distal portion of the cutting blade mechanism can include a cutting edge 30c formed at its terminal, distal end. This cutting edge can be used to cut tissue that is grasped between the jaws when the cutting blade mechanism is distally advanced between the jaws. In an illustrated embodiment, the cutting edge 30c can be arranged at an angle so that the top rib 30a of the cutting blade mechanism 28 extends further distally than the bottom rib 30a of the cutting blade mechanism 28, as shown in FIG. 4A. This can help prevent the tissue from getting impinged by the blade as it is being cut. Still other configurations of the cutting blade are possible and will be known to one of ordinary skill.

Figure 5A:
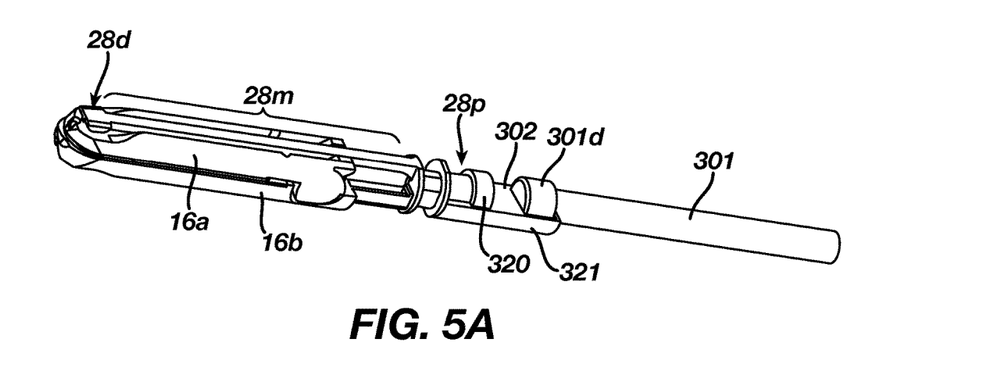
FIG. 5A is a perspective view of the cutting blade mechanism of FIG. 4A associated with the end effector of FIG. 2 and coupled to a push rod of the device of FIG. 1.
Figure 5B:
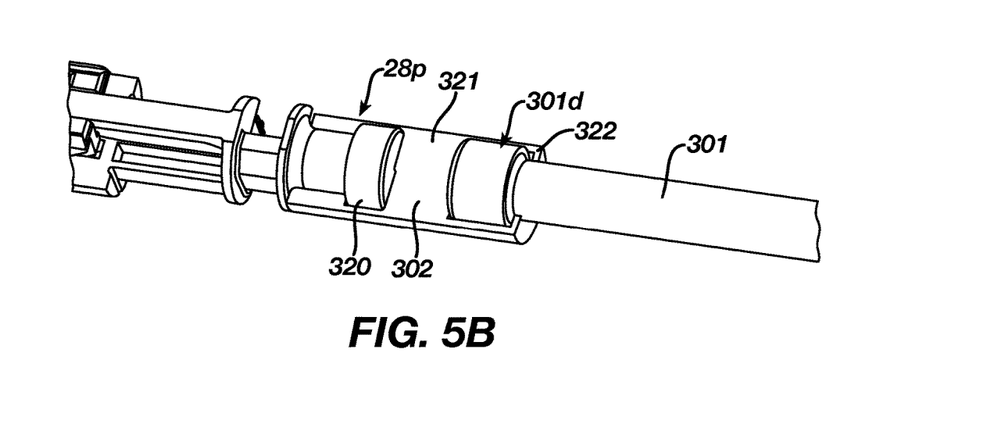
FIG. 5B is an enlarged view of a joint for use in coupling the cutting blade mechanism to the push rod of FIG. 5A.

The proximal portion 28p of the cutting blade mechanism 28 can have any configuration that allows the cutting blade mechanism 28 to be removably coupled to a push rod 301, or other means for mechanical connection to the handle portion. In some embodiments, the proximal portion 28p of the cutting blade mechanism 28 can be coupled to the push rod 301 using a pusher block 302, as shown in FIGS. 5A and 5B. The pusher block 302 can be coupled to the push rod 301, or alternatively, it can be considered a part of the distal end of the push rod 301. In an illustrated embodiment, the proximal end 28p of the cutting blade mechanism 28 forms a male end 320, that is compatible with a female end 321 on the pusher block 302 to allow the cutting blade mechanism 28 to be removably and replaceably attached to the push rod 301. Further, the pusher block 302, on an opposed side, can include a second female end 322, which can be compatible with the male, distal end 301d of the push rod 301. It is generally known in the art that the configuration can also be reversed so that one or both of the male portions can be on the pusher block 302 and one or both of the female portions can be part of the cutting blade mechanism 28 and push rod 301. Likewise, it is also provided that the cutting blade mechanism 28 can be removably coupled directly to the push rod 301, without the use of a pusher block 302.

The cutting blade mechanism 28 provided for herein can have a variety of shapes and configurations, depending, at least in part, on the shapes, sizes, and configurations of the other components with which the blades are being used and the type of procedure in which the cutting blades are being used. For example, in some exemplary embodiments a length of a cutting blade used in conjunction with a tissue cutting device having a shaft with a 5 millimeter diameter can be about 45 millimeters while a length of a cutting blade used in conjunction with a tissue cutting device having a shaft with a 10 millimeter diameter can be about 70 millimeters. More generally, a length of the cutting blade mechanism can be in the range of about 30 millimeters to about 100 millimeters and a width, i.e., the vertical length, of the cutting blade can be in the range of about 1 millimeter to about 10 millimeters, also depending on the size of the shaft in which it is to be disposed. The sizes and shapes of the ribs 30a 30b themselves can likewise vary depending, at least in part, on the shapes, sizes, and configurations of the other components of the device. In some exemplary embodiments, the width $w_t$ of the top rib 30a is in the range of about 0.2 millimeters to about 2 millimeters, the width $w_r$ proximal of the top rib 30a is in the range of about 0.1 millimeters to about 0.8 millimeters, the width $w_b$ of the bottom rib 30b is in the range of about 0.2 millimeters to about 1 millimeter, the width $w_m$ proximal of the bottom rib 30b is in the range of about 0.1 millimeters to about 0.8 millimeters, and the width $w_o$ of the opening 34 is in the range of about 0.2 millimeters to about 1.5 millimeters. In one exemplary embodiment, the width $w_t$ is about 0.6 millimeters, the width $w_r$ is about 0.3 millimeters, the width $w_b$ is about 0.3 millimeters, the width $w_m$ is about 0.15 millimeters, and the width $w_o$ is about 0.4 millimeters.

Generally, a thickness of the cutting blade mechanism can vary based on the surgical procedure that the blade is being used for. In some exemplary embodiments, a thickness of the blade can be in the range of about 0.1 millimeters to about 0.5 millimeters, and in one embodiment the thickness is in the range of about 0.2 millimeters. Further, the cutting blades can be formed from a variety of materials known to those skilled in the art. Generally, the material(s) used to form the cutting blade can be flexible to allow the blade to easily bend without breaking. For example, a metal such as a surgical grade stainless steel (e.g., 17-4) or Nitinol can be used to form the cutting blade.

Different cutting mechanisms can be used for different surgical procedures as needed and as determined by a healthcare provider. Any blade can be interchangeable for use with the end effector as long as the joint is compatible with the joint on the pusher block and the blade can fit into the tracks included on the jaws of the end effector.

Exemplary Surgical Methods

The devices herein can be used to perform a surgical procedure in which tissue is grasped and transected, and optionally sealed using applied energy. A person skilled in the art will appreciate that the procedure can be a minimally invasive procedure or an open surgical procedure. The devices herein can also be used for robotic-assisted minimally invasive or open procedures.

The procedure usually begins by preparing the patient for surgery and making one or more appropriately sized incisions at a desired location. In a minimally invasive procedure, one or more cannulas or trocars (not shown) can be positioned in the incisions to provide access to the surgical site. One or more viewing devices, e.g., scopes, can be placed in one of the incisions to allow medical personnel to view the surgical site from outside the body.

Once the patient is prepared for surgery, a surgical device can be inserted through the incision and/or through the cannula and the end effector can be positioned adjacent to a desired tissue to be treated. In some instances, the tissue to be treated can include one or more layers of blood vessels. As the surgical device is being inserted into the patient, the actuating trigger 20 can be disposed adjacent to the stationary grip 22, so that the jaws 16a, 16b are in a closed position as shown in FIGS. 6 and 8A, thus causing the jaws to have a smaller width for insertion. When the jaws 16a, 16b are positioned adjacent to the tissue to be treated, the actuating trigger 20 can be moved away from the stationary grip 22 and the tissue to be treated can be positioned between the jaws 16a, 16b. Movement of the actuating trigger 20 toward the stationary grip 22 can close the jaws 16a, 16b so that tissue is securely grasped between the jaws 16a, 16b. An angular position of the jaws 16a, 16b can directly correspond to an angular position of the actuating trigger 20 relative to the stationary grip 22. As a user applies an input pressure to the actuating trigger 20 to move it relative to the stationary grip 22, a sensor can optionally measure a distance between the jaws. The processor can calculate a force applied to the tissue grasped between the jaws 16a, 16b. In another embodiment, upon closure of the jaws 16a, 16b, the device 100 can automatically advance a cutting member and/or a compression member toward the jaws 16a, 16b to cut the tissue disposed therebetween. A person skilled in the art will appreciate that energy can be selectively applied to the tissue prior to or during transection of the tissue disposed in the jaws 16a, 16b. Further the button 24 of the handle portion 10 can be operated to supply electrical energy to the electrode 36, and thus to the tissue grasped by the jaws 16a, 16b. The electrical energy can help weld or otherwise seal the tissue.

The surgical device can be inserted into the body using the method described above, but can also apply energy, e.g., RF current, to tissue disposed between the jaws prior to, during, and/or after transection of the tissue. After the cutting member is advanced through the tissue and is retracted proximally, the device 100 can continue to apply energy to the cut tissue or the jaws 16a, 16b can automatically release the tissue. The delivery of energy can occur using any number of techniques known to those skilled in the art, including but not limited to actuation of the actuator button 24 that can complete a circuit to begin energy flow or the switch supplying a radio frequency signal to complete a circuit at some other location in the device to begin energy flow. As shown in FIG. 7, energy flows from the electrode 36, which has a positive charge, and towards the material used to form the jaws 16a, 16b, which has a negative charge. As some of the energy flows through the tissue, it acts to seal the tissue.

In either example, after the cutting is complete, the closure actuator, the firing actuator, and the jaws can release from the compressed/closed positions and can automatically return to their initial position so that the jaw closure, compressing, cutting, etc. can be repeated as many times as desired. A person skilled in the art will recognize a number of other ways by which an end effector and its related components can be operated to transect and/or seal tissue.

Method of Removing Cutting Blade and/or Jaw from Surgical Device

As discussed above, prior to the presently disclosed configurations, it was difficult to clean or remove cutting blades, either jaw and/or electrodes associated with the jaws. The present disclosure, however, makes removal and/or cleaning of these components significantly easier.

In the illustrated embodiment, a user can operate the device to remove a jaw and then optionally remove the cutting blade mechanism. This allows for replacement and cleaning of the jaws and/or the cutting blade mechanism. Further, the operation allows an electrode disposed on one or more jaws to be replaced, which allows for effective reuse of the surgical device because electrodes are typically the first element of the device to wear out and require replacement.

Figure 8B:
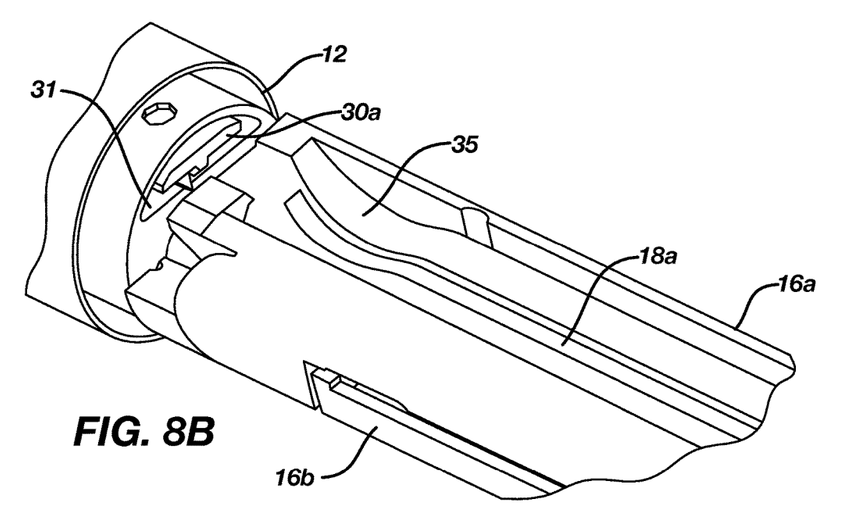
FIG. 8B is a perspective view of the cutting blade mechanism being disposed at a fully retracted position, in which a distal end of the cutting blade mechanism is disposed within a shaft of the device of FIG. 8A.

The jaw and the cutting blade mechanism can be disassociated from the device after the completion of any stroke. A first step in removing the top jaw 16a can be to proximally retract the cutting blade mechanism 28 completely into bore 31 in the shaft 12, thus moving it from the configuration illustrated in FIG. 8A, also referred to herein as an initial position, to the configuration illustrated in FIG. 8B, also referred to herein as an over-extended position because in such a position the trigger 20 can be over-extended with respect to the grip 22. FIG. 8A shows the cutting blade mechanism 28 in the initial position. As discussed above, when the cleaning button 32 is actuated, the cutting blade mechanism 28 can retract proximally, in a direction R, such that the cutting blade mechanism 28 is not visible from a top view of the end effector 14 because the entire distal end of the cutting blade mechanism 28 is disposed in the bore 31 and thus covered by the shaft 12, as shown in FIG. 8B. To prevent accidental retraction of the cutting blade mechanism, and subsequent disengagement of the top jaw, a ramp 35, illustrated in FIG. 8A, is configured such that the application of additional proximal force is required to completely proximally retract the cutting blade mechanism into the shaft 12. For example, in the illustrated embodiment, a slope of the ramp 35 requires only enough additional force to still allow the cutting blade mechanism 28 to be manually retracted. When the proximal force allows the cutting element 28 to pass over the ramp 35, the cutting blade mechanism 28 can be completely proximally retracted into the bore 31, as shown in FIG. 8B. When the cutting blade mechanism 28 is completely retracted, the top jaw 16a can be disengaged from the bottom jaw 16b and can be manually removed from the end effector 14. When the top jaw is removed from the end effector, the top jaw can be cleaned and/or replaced. If an electrode is disposed on the top jaw 16a it can easily be replaced and/or cleaned and repaired as needed when the top jaw 16a is disengaged from the bottom jaw 16b. Removal of the top jaw 16a also allows the user to easily access the bottom jaw 16b for cleaning and/or replacing an electrode or other component(s) associated with the bottom jaw 16b.

Figure 8C:
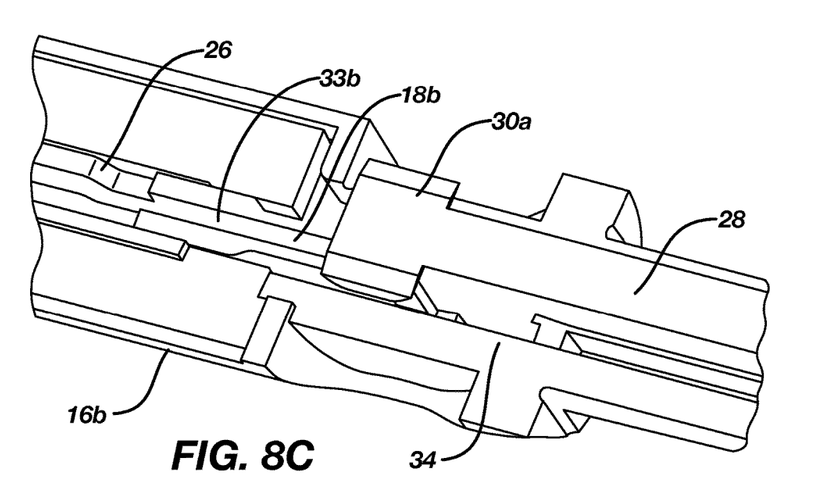
FIG. 8C is a perspective view of the cutting blade mechanism of FIG. 8B being returned to the initial position also illustrated in FIG. 8A with the upper jaw of the device being removed.

Next, if the user desires to remove the cutting blade mechanism 28 for cleaning or replacement, the cutting blade mechanism 28 can be advanced distally in the same manner it is typically advanced distally, i.e., by using the actuating trigger 20 to advance it distally. The user can begin by returning the cutting blade mechanism 28 to its initial position so that its distal end 28d is no longer disposed in the shaft 12. This can be done by depressing the cleaning button 32 again, which can allow the actuating trigger 20, and thus the cutting blade mechanism 28, to return to its initial position, the cutting blade mechanism 28 initial position being illustrated in FIG. 8C. Alternatively, a user can apply a force to the actuating trigger 20 toward the grip 22 so that the actuating trigger, and thus the cutting blade mechanism 28, return to their initial positions.

Figure 8D:
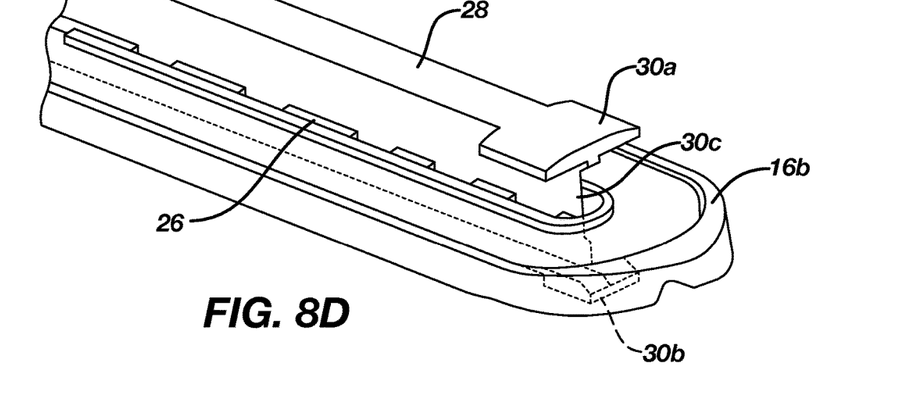
FIG. 8D is a perspective view of the cutting blade mechanism of FIG. 8C in a fully advanced position in which the cutting blade mechanism is advanced to a end of the lower jaw.

Once returned to the initial position, the actuating trigger 20 can be depressed to fully advance the cutting blade mechanism 28 distally, as described herein and as shown in FIG. 8D. When the cutting blade mechanism 28 is completely advanced distally, the pusher block 302 is exposed from the bore 31 in the shaft 12. As a result, the user can disassociate, the proximal end of the cutting blade mechanism 28p from the pusher block 302, thereby disconnecting the cutting blade mechanism 28 from the push rod 301. Alternatively, as part of returning the cutting blade mechanism 28 to its initial position, the action can be continued directly into advancing the cutting blade mechanism 28 distally so that these actions are performed in a single, continuous step.

After de-coupling the cutting blade mechanism 28 from the pusher block 302, the handle portion 10 can be manipulated to return the push rod 301 and pusher block 302 back into the shaft 12, so that they are out of the way, for instance by releasing the actuating trigger 20 so that it moves away from the grip 22. Because the cutting blade mechanism 28, however, is no longer coupled to the push rod 301 and pusher bock 302, proximal retraction of the push rod 301 and pusher block 302 does not cause the cutting blade mechanism 28 to retract. However, it is generally desirable to retract the cutting blade mechanism 28 so that it is not exposed and so that it can be directed through the opening 34 formed in the bottom jaw 16b to disassociate the cutting blade mechanism 28 from the rest of the device. Thus, the user can hold a proximal portion 28p of the cutting blade mechanism 28 and manually retract it towards the handle portion 10. In some instances, the user may return the proximal portion 28p directly into the shaft 12. In other instances, the user may return the proximal portion 28p to a location adjacent to but outside of the shaft 12. By keeping the cutting blade mechanism 28 outside of the shaft, it may provide more flexibility to the user as the user manipulates the rib 30b through the opening 34, but keeping the cutting blade mechanism inside of the shaft 12 can be useful in keeping the device 10 more compact. A person skilled in the art will recognize which method is most appropriate based on the particular situation.

Figure 8E:
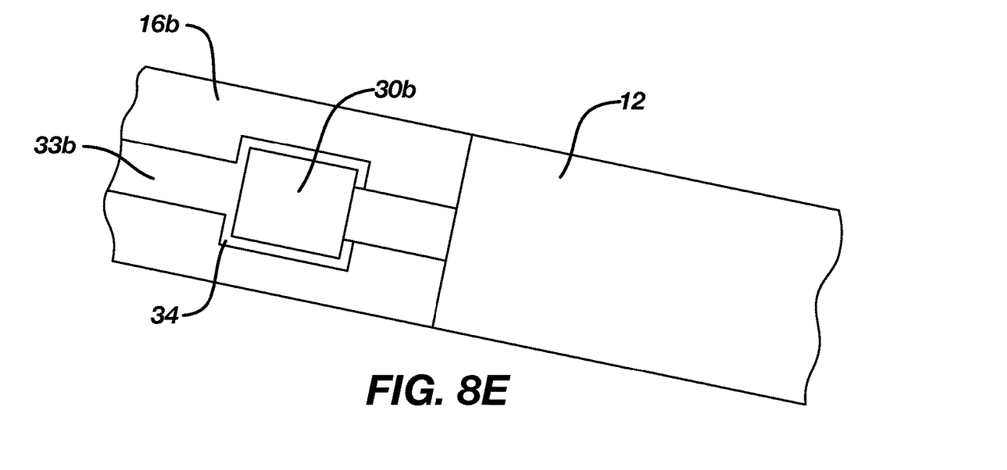
FIG. 8E is a perspective view of the cutting blade mechanism of FIG. 8D in a removal position in which the cutting blade mechanism is retracted proximally and a rib of the cutting blade mechanism is passed through an opening formed in the lower jaw so that the cutting blade mechanism can be disassociated from the jaws.

As shown in FIG. 8E, the rib 30b can retract proximally through the jaws 16a, 16b and then can be passed through the opening 34 in the bottom jaw 16b once the rib 30b is aligned with the opening 34. More particularly, the cutting blade mechanism 28 can be removed from the jaws 16a, 16b by manually lifting the distal end 28d of the cutting blade mechanism 28 away from the bottom jaw 16b and completely disconnecting the cutting blade mechanism 28 from the end effector 14 of the surgical device 100. Once disengaged from the end effector 14, the cutting blade mechanism can be manually removed from the device. While the upper jaw 16a and/or cutting blade mechanism 28 are disengaged from the end effector 14 of the device 100, the user is able to easily clean, sharpen, and/or replace all of the elements of the end effector 14.

During assembly of a new upper jaw onto the device, or reassembly of the removed upper jaw 16a onto the device 10 after cleaning or electrode replacement, if the cutting blade mechanism 28 was removed from the end effector 14, the cutting blade mechanism 28 can be replaced by first depressing the actuating trigger 20 to expose the pusher block 302 from the shaft. Next, the proximal end 28p of a new or cleaned cutting blade mechanism 28 can be engaged with the pusher block 302. The top jaw can be replaced or re-attached after the cutting blade mechanism 28 has been replaced and retracted completely into the shaft. If the cutting blade mechanism 28 was not replaced, it still is retracted completely into the shaft 12 to allow the upper jaw 16a to be pivotally coupled to the lower jaw 16b. Retracting the cutting blade mechanism 28 can be accomplished again by depressing the cleaning button 32 to distally advance the actuating trigger 20 into its over-extended position, which in turn causes the cutting blade mechanism 28 to retract completely into the shaft 12. Then a new or cleaned upper jaw 16a can be placed on top of the bottom jaw 16b, with the protrusions 40c, 40d of the upper jaw 16a being seated in the grooves 41c, 41d of the lower jaw 16b. The actuating trigger 20 can be depressed to distally advance the cutting blade mechanism 28 out of the shaft 12 so that it engages the upper and lower jaws 16a, 16b, thereby reassembling the end effector 14 for further grasping and/or sealing.

The devices disclosed herein can be designed to be disposed of after a single use, or they can be designed to be used multiple times. In either case, however, the device can be reconditioned for reuse after at least one use. Reconditioning can include any combination of the steps of disassembly of the device including removal of the top jaw and/or cutting blade mechanism, followed by cleaning or replacement of particular pieces including the jaws, electrodes, and cutting blade mechanism, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the devices described herein will be processed before surgery. First, a new or used instrument is obtained and if necessary cleaned. The instrument can then be sterilized. In one sterilization technique, the instrument is placed in a closed and sealed container, such as a plastic or TYVEK® bag. The container and its contents are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, steam.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical device, comprising:
   first and second jaws, the first jaw being removably coupled to the surgical device and the second jaw having a through-hole formed in a proximal portion thereof; and
   a cutting blade slidably coupled to the first and second jaws, the cutting blade having opposed first and second ribs disposed at a distal portion of the cutting blade, the first and second ribs being configured to move in a longitudinal direction to cause axial translation of the cutting blade relative to the elongate shaft,
   wherein, once the first jaw is removed from the surgical device, the second rib is configured to move in a first longitudinal direction to align with the through-hole of the second jaw, and once aligned, the second rib is configured to move in a lateral direction to pass through the through-hole so as to remove the cutting blade from the surgical instrument.

2. The surgical device of claim 1, further comprising
   a handle portion; and
   a shaft extending distally from the handle portion, a distal end of the shaft being fixedly coupled to a proximal end of the second jaw.

3. The surgical device of claim 2, further comprising a push rod disposed in the shaft, wherein a proximal end of the cutting blade is removably coupled to a distal end of the push rod.

4. The surgical device of claim 2, wherein the cutting blade is configured to fully retract within the shaft to disengage the first and second ribs from the first and second jaws so as to allow the first jaw to be decoupled from the surgical device.

5. The surgical device of claim 1, wherein each of the first and second jaws has a centrally disposed channel formed therein, and the cutting blade further comprises a main vertical body extending between the channels of the first and second jaws and configured to translate therethrough, the main vertical body having a cutting edge formed on a distal end thereof, between the first and second ribs.

6. The surgical device of claim 5, wherein a width of the first rib and a width of the second rib is greater than a width of the main vertical body, each width being perpendicular to a longitudinal axis extending through the main vertical body in a proximal to distal direction and perpendicular to a height of the main vertical body that extends vertically between the first and second jaws.

7. The surgical device of claim 1, wherein the first jaw includes a tissue engaging portion having an electrode disposed thereon.

8. The surgical device of claim 1, further comprising a handle assembly having a stationary grip and a trigger, the trigger being operably coupled to the cutting blade,
   wherein the trigger is configured to move between a first resting position at which a distal end of the cutting blade is disposed at a proximal end of the first and second jaws and a second cutting position at which the distal end of the cutting blade is disposed proximate to a distal end of the first and second jaws, the trigger being located more proximate to the stationary grip in the second cutting position than in the first resting position, and
   wherein the trigger is further configured to move to a third, over-extended position at which the distal end of the cutting blade is disposed proximal of the proximal end of the first and second jaws, the trigger being located more proximate to the stationary grip in the first resting position than in the third, over-extended position.

9. A surgical device, comprising:
a shaft extending distally from a handle portion, the handle portion having an actuating trigger, a stationary grip, and a button;
a first jaw having a first surface and an opposed second surface, the first surface having a tissue engaging portion disposed at least at a distal portion of the first jaw, and the first jaw having an opening formed in a proximal portion of the first jaw, the opening extending through the first jaw from the first surface to the second surface;
a second jaw removably and pivotally coupled to the first jaw, the second jaw having a first surface and an opposed second surface, the first surface having a tissue engaging portion disposed at least at a distal portion of the second jaw, the first surfaces of the first and second jaws being opposed to each other to grasp tissue therebetween; and
a cutting blade slidably coupled to the first and second jaws, the cutting blade having opposed first and second ribs disposed at a distal portion of the cutting blade, the first rib being configured to slide along the second surface of the first jaw and the second rib being configured to slide along the second surface of the second jaw such that distal advancement of the first and second ribs along the second surfaces of the first and second jaws moves the second jaw towards the first jaw into a closed position, and proximal retraction of the first and second ribs along the second surfaces of the first and second jaws allows the second jaw to pivot away from the first jaw into an open position,
wherein a perimeter of the first rib is less than a perimeter that defines the opening in a proximal end of the first jaw such that the first rib is configured to be selectively passed through the opening to disassociate the cutting blade from the first jaw, and
wherein the actuating trigger being operably coupled to the cutting blade such that advancing the actuating trigger towards the stationary grip advances the cutting blade distally and advancing the actuating trigger away from the stationary grip retracts the cutting blade proximally, and the button is operably coupled to the actuating trigger such that the button is configured to initiate an overextended mode in which the actuating trigger advances further away from the stationary grip to dispose the distal end of the cutting blade in the shaft.

10. The surgical device of claim 9, further comprising a push rod disposed in the shaft, wherein a proximal end of the cutting blade is removably coupled to a distal end of the push rod.

11. The surgical device of claim 9, wherein a distal end of the cutting blade is configured to be disposed in the shaft such that the second rib does not engage the second surface of the second jaw and allows the second jaw to be decoupled from the first jaw.

12. The surgical device of claim 9, wherein each of the first and second jaws has a centrally disposed channel formed therein, and the cutting blade further comprises a main vertical body extending between the channels of the first and second jaws and configured to translate therethrough, the main vertical body having a cutting edge formed on a distal end thereof, between the first and second ribs.

13. The surgical device of claim 12, wherein a width of the first rib and a width of the second rib is greater than a width of the main vertical body, each width being perpendicular to a longitudinal axis extending through the main vertical body in a proximal to distal direction and perpendicular to a height of the main vertical body that extends vertically between the first and second jaws.

14. The surgical device of claim 9, wherein the tissue engaging portion of the second jaw further comprises an electrode.

* * * * *